United States Patent [19]

Bayevsky et al.

[11] Patent Number: 5,955,128
[45] Date of Patent: *Sep. 21, 1999

[54] SYSTEM AND METHOD FOR STANDARDIZING A CONCENTRATE

[75] Inventors: Michael Bayevsky, St. Louis Park; M. Douglas Rolland, Willmar, both of Minn.

[73] Assignee: Relco Unisystems Corporation, Willmar, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/823,419

[22] Filed: Mar. 25, 1997

[51] Int. Cl.$^6$ ............................. A23C 1/00; G01N 33/00
[52] U.S. Cl. ........................ 426/231; 210/650; 210/739; 426/491; 426/495
[58] Field of Search .................................. 426/231, 491, 426/495, 36; 210/650, 651, 739, 745, 746

[56] References Cited

U.S. PATENT DOCUMENTS

| | | | |
|---|---|---|---|
| 3,983,257 | 9/1976 | Malmberg et al. | 426/231 |
| 4,800,808 | 1/1989 | Lidman | 210/650 |
| 5,009,794 | 4/1991 | Wynn | 210/739 |
| 5,338,553 | 8/1994 | Johnson et al. | 426/36 |
| 5,591,469 | 1/1997 | Zettier | 426/231 |

OTHER PUBLICATIONS

Kennedy et al, Food Chemistry, vol. 18(2), 1985, pp. 95–112.
Brochure from On–Line Instrumentation, Inc. entitled "Automatic Standardization".
Brochure from Filtration Engineering Company, Inc. entitled "Information".
Brochure from Foss Food Technology entitled "State of the Art Process Control Automatic In–Line Standardization".
Brochure from Foss Food Technology entitled "Optimize Your Dairy Production".

*Primary Examiner*—George Yeung
*Attorney, Agent, or Firm*—Merchant & Gould P.C.

[57] ABSTRACT

A method of forming a concentrate, the concentrate having a predetermined concentration of a component in the concentrate. The method comprising the steps of: filtering a fluid thereby separating the fluid into a permeation and the concentrate; determining the concentration of the component in the concentrate; and if concentration of the component is greater than a predetermined concentration, decreasing the concentration of the component to the predetermined concentration. Dilution is achieved by feeding permeate into the concentrate or by controlling a pressure differential within a filter.

16 Claims, 4 Drawing Sheets

SYSTEM AND METHOD FOR STANDARDIZING A CONCENTRATE

TECHNICAL FIELD

The present invention relates to a system and method for producing a concentrate, and more particularly, to a system and method for standardizing a concentrate.

BACKGROUND

In the production of dairy products such as cheese, a milk product is separated into whey and curd. The curd is used to produce the cheese and the whey is a by product rich in lactose, minerals, vitamins, and protein. Rather than discarding the whey as waste, many producers will use it to make other useful products. An example of such a product is whey protein concentrate, which is used as an additive in food items to enhance the food's nutritional value.

Whey protein concentrate is typically produced by filtering the whey to form a concentrate and a permeate, both of which are fluid. The concentrate includes water and solid components, including a protein. The concentration of protein in the concentrate is greater than the concentration of protein in the original whey. After filtering is complete, the producer removes substantially all of the water from the concentrate to produce a powdered whey protein concentrate. Alternatively, the producer can sell a concentrate liquid and forgo the step of removing water from the concentrate. The protein concentration is determined by the ratio between the amount of protein in the concentrate and the total amount of solid components in the concentrate.

The standard in the dairy industry is to produce whey protein concentrate having a specification that lists the protein concentration at 34% or 50%. The producers also sell a high protein product that has a specification that lists the protein concentration between 80% and 85%.

Current processing technology has a significant shortcoming because there is not an efficient method of measuring and regulating the production process. For example, test equipment that is used on-site is usually limited to a refractometer, which can only measure the total amount of solids in the sample. Thus, the producer does not have the capacity to measure the ratio between the protein and the other components in the concentrate. Rather, the producer must rely on the accuracy and reliability of the filtering equipment, which may be imprecise itself.

A producer can take samples to a lab to obtain more accurate chemical testing or use more precise equipment. However, workers must manually take these samples and carry them to a laboratory for testing. Such testing is inefficient and can present logistical difficulties. As a result, a producer typically takes only a few samples each day. A problem arises in this situation because calibration of the system can falter during the long period between testing and thus produce a large amount of whey protein concentrate that has fallen below the protein concentration listed in the product specification.

In order to account for all of these problems and still meet the product specification, the producers typically produce a whey protein concentrate that has a protein concentration higher than the specification. For example, if the producer is processing a whey protein concentrate to meet the specified concentration of 34% protein, it may produce a product having a protein concentration as high as 37%.

Because the producers sell its whey protein concentrate as though it has a concentration of only 34%, it is giving away a significant amount of protein—3 pounds of protein for every 100 pounds of concentrate that is sold. If the concentrate sells for $0.65 a pound and the manufacture produces 55,000 pounds a day, which is a typical price and production capacity for a dairy plant, it is giving away over 1000 pounds of product each day. Giving away this much protein results in lost profits each year that exceed several hundred thousand dollars. This loss is significant.

These shortcomings found in current processes for producing a whey protein concentrate also exist in the production of other types of concentrates in the dairy and food industries. They may also exist in other industries that produce a concentrate of some form.

Therefore, there is a need for a system and method for producing a concentrate that has a concentration that matches the specification. There is also a need for a system and method that will match the concentration specification regardless of how far the filter operates above the specification. There is another need for a system and method for automatically determining the concentration of a component within a concentrate.

SUMMARY

The present invention is directed to a method of forming a concentrate. The concentrate has a predetermined concentration of a component in the concentrate. The method comprises the steps of: filtering a fluid thereby separating the fluid into a permeation and the concentrate; determining the concentration of the component in the concentrate; and if concentration of the component is greater than a predetermined concentration, decreasing the concentration of the component to the predetermined concentration.

The present invention is also directed to a system for producing a concentrate from a fluid containing a component. The system comprises a filter configured to receive the fluid and to separate the fluid into the concentrate and a permeate. A first conduit is in fluid communication with the filter and arranged to receive the concentrate. A second conduit is in fluid communication with the first conduit and configured to draw concentrate from the first conduit. A measuring device is in fluid communication with the second conduit and is configured to measure the concentration of the component within the concentrate. Control means are in fluid communication with the filter. The control means are configured to decrease concentration of the concentrate if the concentration is greater than a predetermined concentration.

DETAILED DESCRIPTION

Figure 1:
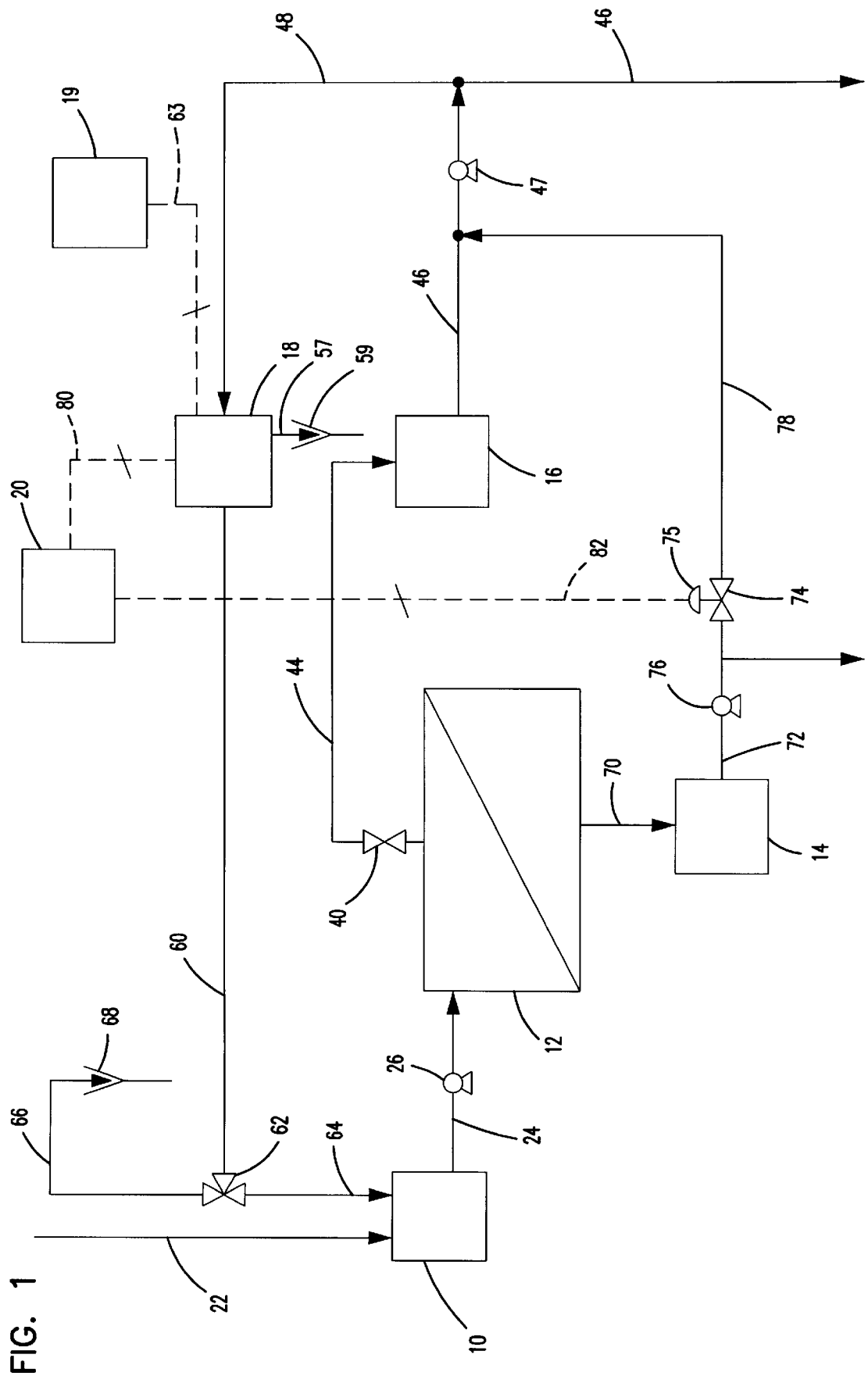
FIG. 1 is a schematic view of a system for producing a concentrate.

A preferred embodiment of the invention will be described in detail with reference to the drawings, wherein like reference numerals represent like parts and assemblies throughout the several views. Reference to the preferred embodiment does not limit the scope of the invention, which is limited only by the scope of the claims attached hereto.

In general, the present invention relates to a system and method for standardizing the concentration of a component that is in a concentrate. The concentrate is produced by filtering a fluid that has at least one component. Filtering the fluid produces a permeate and the concentrate. After filtering, the concentration of the component in the concentrate is measured and then diluted if it is above a predetermined level.

The concentration can be controlled in a number of different ways. For example, some of the permeate can be blended back into the concentrate. Alternatively, if the system utilizes ultrafiltration, a fluid is injected into the filter and pressurized in order to force the permeate through a semipermeable membrane thereby producing the concentrate. The amount of pressure is controlled in order to regulate the resulting concentration of the component in the concentrate.

This system and method has many advantages. For example, the producer can match the concentration specification of the whey protein concentrate regardless of how far the protein concentration in the concentrate is above the specification. The present system also permits the concentration of the component to be quickly adjusted once a deviation from the specification is detected, which minimizes any error. A related advantage is that the amount of the component that exceeds the standard and is thus given away to a customer is minimized. As a result, the producer's profit is increased because it can charge for all of the component that is distributed.

The detailed description describes a system and method for use in the dairy industry to produce whey protein concentrate. The description uses the production of whey protein concentrate only for the purpose of example. Alternative embodiments of the present invention can be used to produce concentrates of other materials that are found in a dairy product such as lactose, various minerals, fattysolids, non-fat solids, and the like. The present invention also can be used in other industries to produce concentrates of materials that are not dairy-based.

Referring now to FIG. 1, one possible embodiment of the present invention includes a feed balance tank 10, a filter 12, a permeate balance tank 14, a concentrate balance tank 16, a measuring device 18 for measuring the concentration of a component in a fluid, a chart recorder 19, and a programmable logic controller 20. The balance tanks are sized to hold enough fluid to provide about two minutes worth of flow.

An input conduit 22 feeds the input fluid or product to the feed balance tank 10. Such a conduit can be a pipe, tube, duct, channel, or any other structure that provides a path for fluid to flow into the feed balance tank. A feed conduit 24 carries the input fluid from the feed balance tank 10 to the filter 12. A feed pump 26 pumps the fluid through the feed conduit 24.

Figure 2:
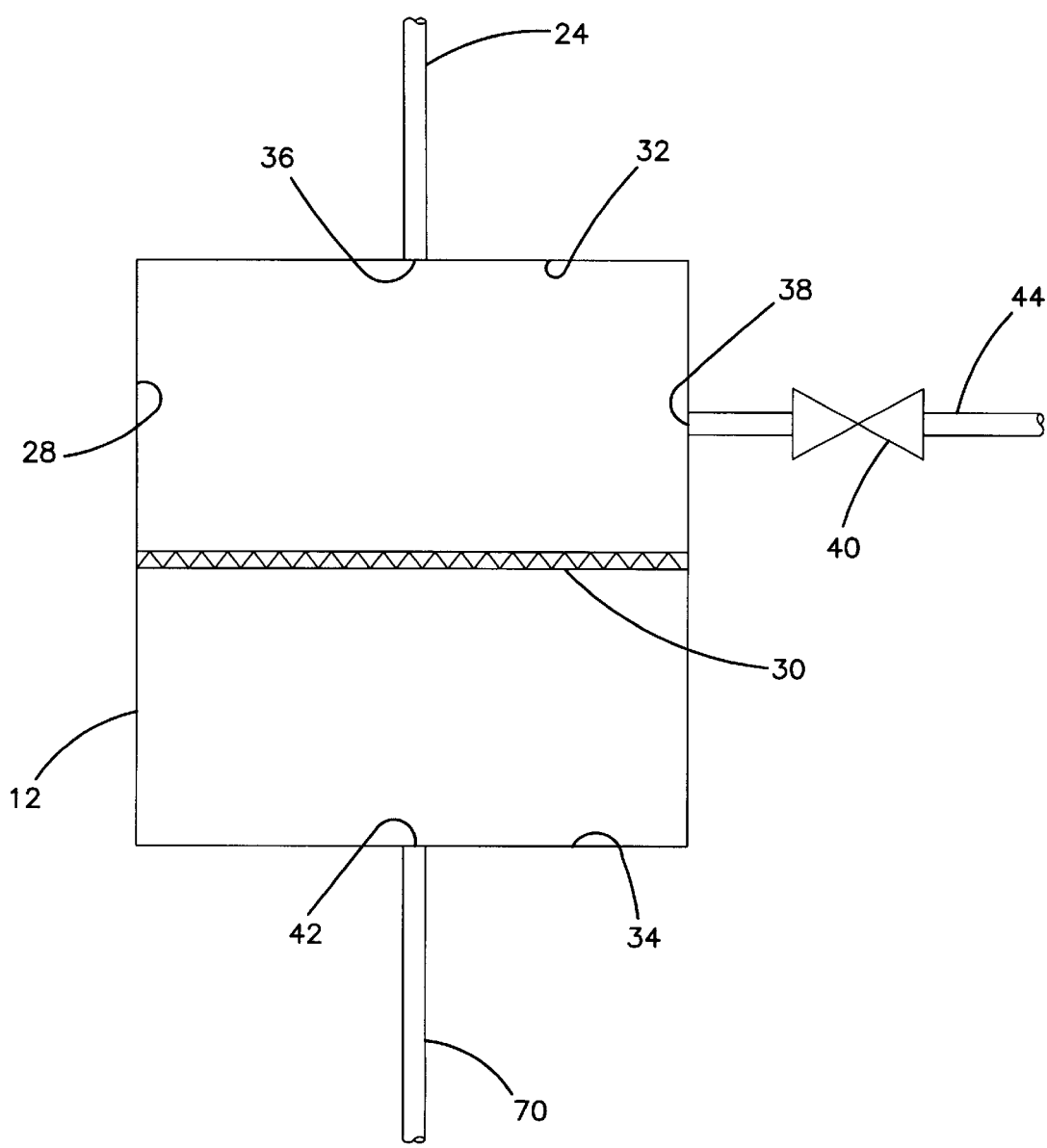
FIG. 2 illustrates a filter that is shown in FIG. 1.

Referring to FIG. 2, one possible embodiment of the present invention utilizes ultrafiltration. In this embodiment, the filter 12 has a chamber 28 and a semipermeable membrane 30 that divides the chamber 28 into two sub-chambers, a concentrate sub-chamber 32 and a permeate sub-chamber 34. An input port 36 receives fluid from the feed conduit 24 and is in fluid communication with the concentrate sub-chamber 32. A first output port 38 provides fluid communication between the concentrate sub-chamber 32 and a back-pressure valve 40. A second output port 42 provides an output from the permeate sub-chamber 34. Although ultrafiltration is described, the system and method can utilize any other type of filter that separates a concentrate from a fluid.

In use, the fluid is pumped into the concentrate sub-chamber 32 and is pressurized by the constant pumping action of the pump 26. A permeate then passes through the semipermeable membrane 30 and into the permeate sub-chamber 34. A concentrate remains in the concentrate sub-chamber 32. The concentrate is formed from components that are too large to pass through the pores of the semipermeable membrane 30. The concentrate also includes fluid and other components that do not get forced through the semipermeable membrane 30 by the pressure within the concentrate sub-chamber 32. Thus, the concentration of the components in the concentrate depends on the nature of the membrane and the pressure within the concentrate sub-chamber 32, which is created by the feed pump 26 and the back-pressure valve 40.

Variations and changes in the microporous membrane 30, feed pump 26, and back-pressure valve 40 affect the pressure in the concentrate sub-chamber 32 and thus the concentration of protein within the concentrate that is produced by the filter 12. Such variations and changes may occur over time as the system is used and the components wear out.

In the past, these components were periodically checked and adjusted to make sure that the system was operating within a set range of parameters. The present invention is advantageous because it eliminates the frequency with which these components need to be checked and readjusted, thereby saving time and money.

Referring back to FIG. 1, a first concentrate conduit 44 provides fluid communication between the back-pressure valve 40 and the concentrate balance tank 16. In turn, a second concentrate conduit 46 provides fluid communication between the concentrate balance tank 16 and an evaporator (not shown) where liquid is removed from the concentrate. A concentrate pump 47 pumps the concentrate through the second concentrate conduit 46 and to the evaporator. The concentrate is then transported to a drier (not shown) to remove substantially all of the remaining liquid and form a powdered whey protein concentrate.

Other types of process equipment can be used in lieu of an evaporator and a drier to remove liquid from the concentrate. For example, the concentrate could be packaged as a concentrate liquid without being processed by an evaporator and a drier.

Figure 3:
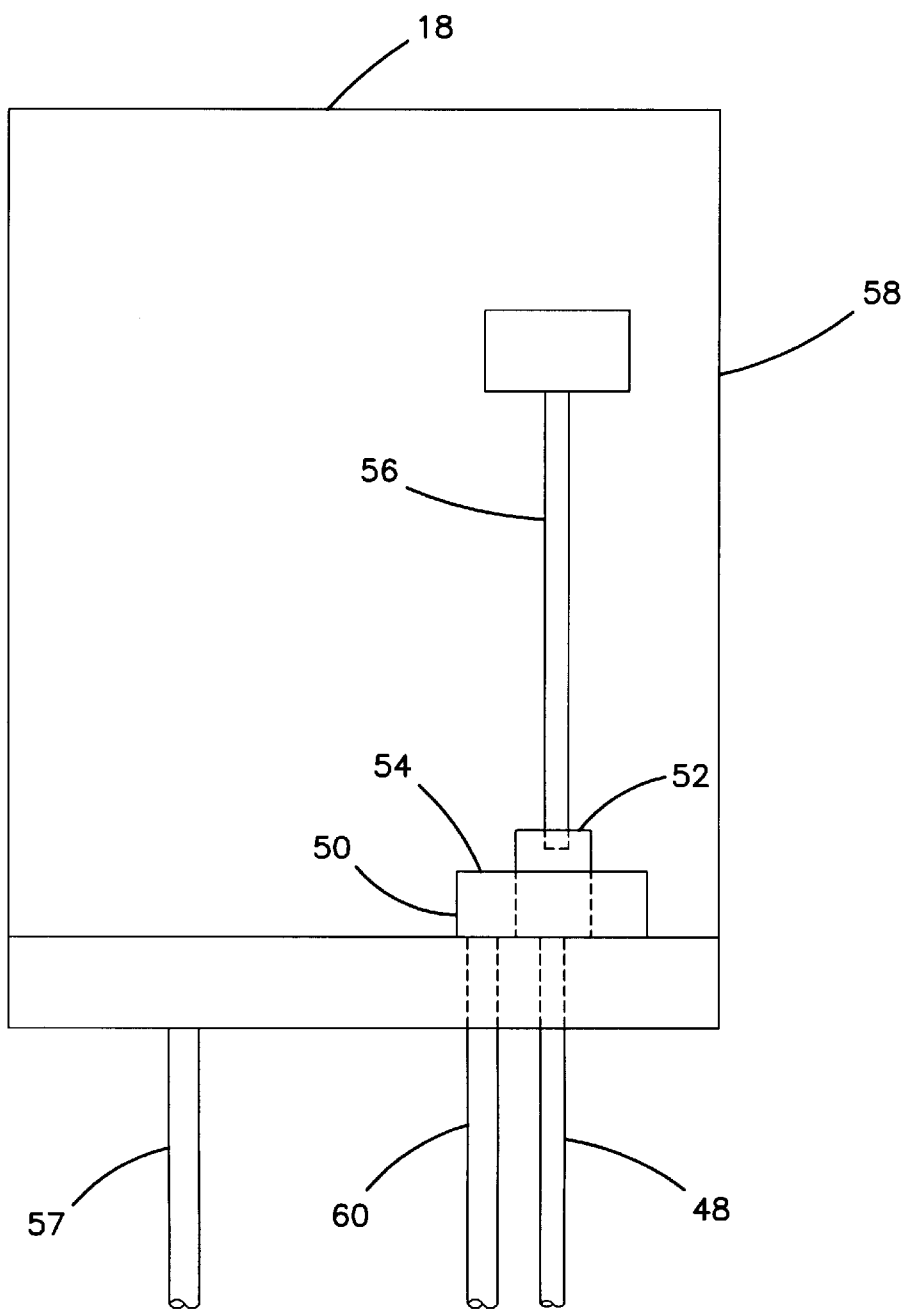
FIG. 3 illustrates a measuring device that is shown in FIG. 1.

A sample draw conduit 48 provides fluid communication between the second concentrate conduit 46 and the measuring device 18. Referring to FIG. 3, the measuring device 18 has a reservoir 50 that has an inner bowl 52 positioned within a concentric outer bowl 54. The sample draw conduit 48 is in fluid communication with the inner bowl 52 and continuously feeds concentrate into the inner bowl 52 at a rate of about 100 ml to about 200 ml per minute. The concentrate overflows the top edge of the inner bowl 52 and spills into the outer bowl 54. As a result, the concentrate that is within the inner bowl 52 is continuously refreshed.

A pipette 56 projects from the body 58 of the measuring device 18 and into the inner bowl 52. Additionally, a sample drain conduit 57 extends between the measuring device 18 and a sample drain 59. When making a measurement, the measuring device 18 draws a fresh sample of the concentrate through the pipette 56 and measures the concentration of components that are within the sample. The sample is then discharged though the sample drain conduit 57. In order to maintain optimum accuracy, the measuring device 18 is programmed to automatically draw a fresh sample and make a measurement every minute.

An advantage of making measurements once every minute is that the concentration of the protein can be accurately controlled and any error that creeps into the system is quickly corrected. Nevertheless, the interval between measurements of a sample can vary in other embodiments. For example, the measuring device 18 might make a measurement once every thirty seconds, once every two minutes, once every five minutes, or once every half an hour.

When making a measurement, the measuring device 18 determines the amount of protein and the amount of total solids that are in the sample. The measuring device 18 then calculates the ratio between the protein and the total solids. This ratio corresponds to the protein concentration in the powdered form of whey protein concentrate.

In an alternative embodiment, the measuring device 18 can measure a variety of different components or combinations of components other than protein and total solids. The measuring device 18 also can be programmed to make a variety of comparisons or calculations. For example, the measuring device can be programmed to calculate the ratio between any combination of components such as the ratio between two components or the ratio between a component and a combination of components other than the total solids.

The chart recorder 19 is electrically connected to the measuring device 18 via a first electrical interface 63. The chart recorder 19 can record a variety of information that is measured or calculated by the measuring device 18 such as the concentration of protein. In an alternative embodiment, the measuring device 18 interfaces with a computer that can store various measurements and calculations. The computer can then perform various types of analyses using this information.

Recording such information has several advantages. For example, a worker can detect a failure of the semipermeable membrane 30 if there is a sudden change in the concentration of protein. Also, a historical analysis can detect gradual changes in the performance of the semipermeable membrane 30. These changes can be monitored and used to predict when a semipermeable membrane 30 must be replaced as a part of a preventative maintenance program.

In one possible embodiment of the present invention that is used for producing whey protein concentrate, the measuring device 18 is either the MilkoScan S 54 A dairy analyzer or the MilkoScan S 54 B dairy analyzer, both of which measure fat, protein, lactose, non-fat solids, and total solids. The MilkoScan dairy analyzers project an infrared beam of light though the sample. Different components will either absorb or reflect different frequencies of light in the infrared spectrum. The MilkoScan analyzers use this information to determine the concentration of components contained in the sample.

The MilkoScan analyzers are modified to add the reservoir 50. The programming of the MilkoScan analyzers is also modified to automatically draw a sample and make a measurement without the need for human intervention to initiate each cycle. The MilkoScan analyzers are manufactured by Foss Food Technology Corporation of Eden Prairie, Minn. Although the MilkoScan analyzers are described, other embodiments of the present invention can use measuring devices from other manufactures, or can use measuring technologies other than infrared beams.

Referring back to FIG. 1, a discharge conduit 60 provides fluid communication between the outer bowl 54 and a valve 62. A feedback conduit 64 provides fluid communication between the valve 62 and the feed balance tank 10. A drain conduit 66 provides fluid communication between the valve 62 and a drain 68. A producer can adjust the valve 62 so that the overflow concentrate from the measuring device 18 is either fed back into the feed balance tank 10 and reprocessed or is sent to the drain 68 and discarded as waste. The producer might discard the overflow concentrate if the process is used to produce a highly regulated product that must meet exacting standards for sanitation. In other embodiments of the present invention, the overflow concentrate can be fed into other portions of the system such as the filter 12; the concentrate balance tank 16; or any conduit that provides a path for the fluid, concentrate, or permeate.

A first permeate conduit 70 provides fluid communication between the permeate sub-chamber 34 of the filter 12 and the permeate balance tank 14. A second permeate conduit 72 then provides a path to discharge permeate from the system. In one possible embodiment, the second permeate conduit 72 provides fluid communication from the permeate balance tank 14 to additional process equipment such as an evaporator. The second permeate conduit 72 is in fluid communication with a dilution valve 74 and with a permeate pump 76 for pumping the permeate. The dilution valve 74 is downstream from the permeate pump 76. In turn, a dilution conduit 78 provides fluid communication between the dilution valve 74 and the second concentrate conduit 46 at a point that is upstream from the concentrate pump 47. This configuration is advantageous because the concentrate pump 47 provides dynamic mixing of the permeate and the concentrate as well as a motive force for the concentrate flowing from the concentrate balance tank 16.

The dilution valve 74 is a precise valve that has a orifice with a width between about ¼ inch and about ⅜ inch. The valve also has a plug with a taper that is between about 2° and about 6°. An example of such a valve is model # FCV-E02-.250-04, which is manufactured by Relco Unisystems Corporation of Willmar, Minn. The dilution valve 74 has an electronic actuator 75, which provides quick and accurate adjustments in the plug and hence the flow of fluid.

The programmable logic controller 20 is interfaced with the measuring device 18 and the actuator of the dilution valve 74 via second and third electrical interfaces 80 and 82, respectively. The measuring device 18 communicates the concentration of the protein within the sample to the programmable logic controller 20, which then compares the concentration to a set point. The set point corresponds to a concentration of the components that the producer desires the product to have. In the embodiment described herein, the component is protein and the final product is whey protein concentrate, although the invention is not limited to standardizing whey protein concentrate.

If the measured concentration of protein is above the set point, the programmable logic controller 20 will control the electronic actuator 75 to open the dilution valve 74 a certain amount and thus increase the dilution of the concentrate. Likewise, if the measured concentration of protein is below the set point, the programmable logic controller 20 will control the electronic actuator 75 to close the dilution valve 74 a certain amount and thus decrease the dilution of the concentrate. If the measured concentration of the component matches the set point, the programmable logic controller 20 will not actuate the electronic actuator 75. The amount that the dilution valve 74 is adjusted (i.e., opened or closed) is proportional to the deviation between the measured concentration and the set point. The programmable logic controller 20 repeats this process every time that it receives a measurement of the protein concentration from the measuring device 18.

The programmable logic controller 20 determines how much to open or close the valve using a proportional integral derivative (PID) control loop. In order to utilize the PID control loop, the programmable logic controller 20 is loaded with the dimensions of the valve so that it can calculate the flow rate through the valve. Using a PID control loop is advantageous because it provides continuous control of the protein concentration. PID control loops are well known to those skilled in the art. One possible embodiment of the present invention uses an SLC-500 programmable logic controller, which is manufactured by Allen-Bradley Company, Inc.

An advantage of the invention shown in FIG. 1 is that a producer can implement it by retrofitting its existing process for producing whey protein concentrate. As a result, this system can be implemented without the expense of installing an entire new system. Nevertheless, this embodiment can also be used in a new system as well as an existing system.

Figure 4:
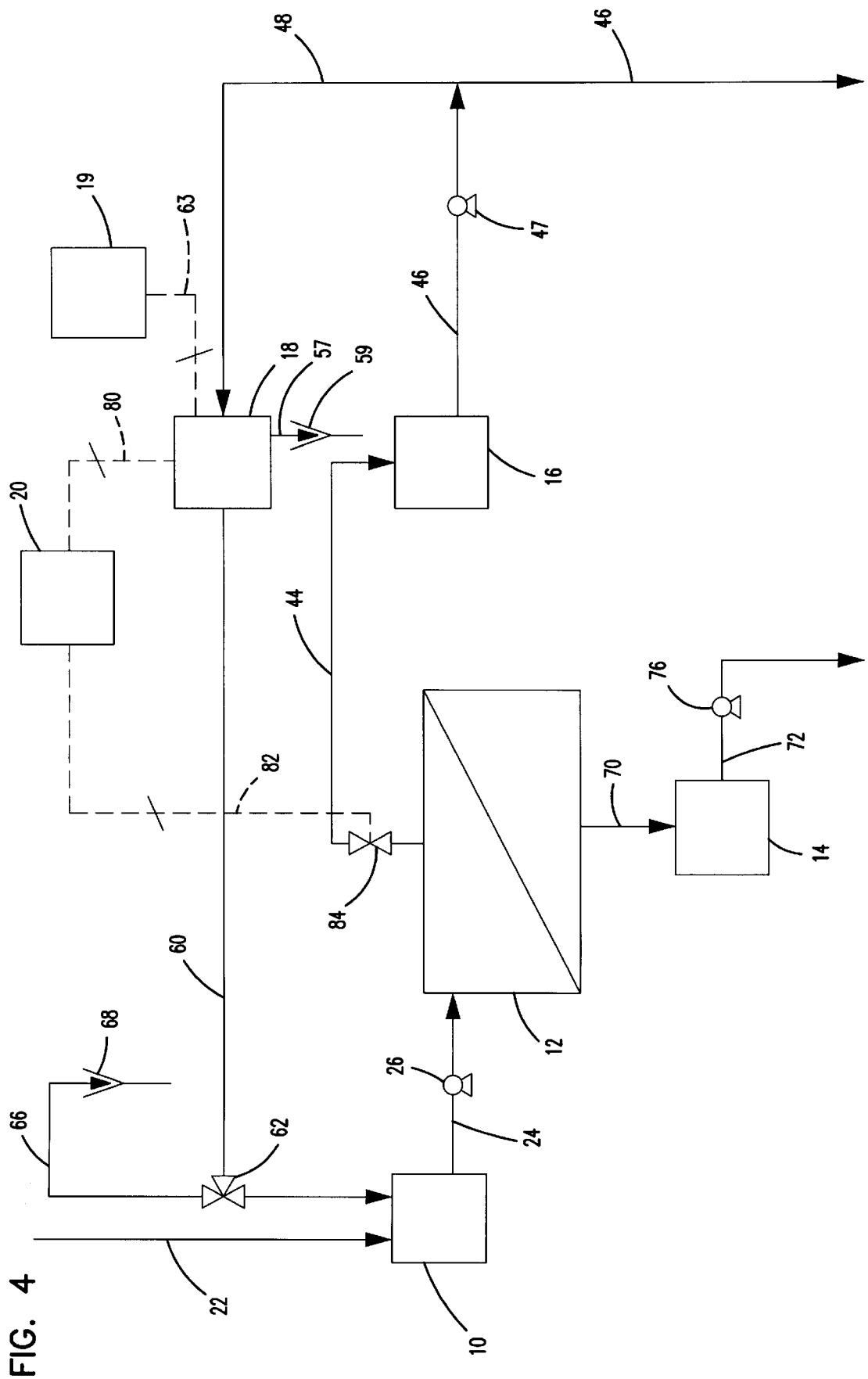
FIG. 4 illustrates an alternative embodiment of the system shown in FIG. 1.

Referring now to FIG. 4, an alternative embodiment is substantially similar to the embodiment shown in FIG. 1, and includes the feed balance tank 10, the filter 12, the permeate balance tank 14, the concentrate balance tank 16, the measuring device 18, the chart recorder 19, the programmable logic controller 20, the input conduit 22, the feed conduit 24, the feed pump 26, the first and second concentrate conduits 44 and 46, the concentrate pump 47, the sample draw conduit 48, the sample drain conduit 57, the sample drain 59, the discharge conduit 60, the valve 62, the feedback conduit 64, the drain conduit 66, the drain 68, the first and second permeate conduits 70 and 72, and the permeate pump 76. The primary difference is that the back-pressure valve 40 of the embodiment shown in FIG. 1 is replaced with an electronic back-pressure valve 84 that is substantially similar to the dilution valve 74 described above. As a result, the electronic back-pressure valve 84 can be controlled to accurately regulate the pressure in the concentrate sub-chamber 32. In this embodiment, the electronic back-pressure valve 84 also replaces the dilution valve 74 and the dilution conduit 78. Alternatively, the programmable logic controller 20 could control the feed pump 26 in order to regulate pressure within the concentrate sub-chamber 32.

Changing this pressure differential causes a change in the concentration of the protein within the concentrate. For example, increasing the pressure will force more fluid and components through the semipermeable membrane 30, which will increase the concentration of the protein. Likewise, decreasing the pressure will force less fluid and components through the semipermeable membrane 30, which will decrease the concentration of the protein.

In use, if the programmable logic controller 20 determines that the concentration of the protein is above the set point, it will control the electronic back-pressure valve 84 to open and decrease the pressure in the concentrate sub-chamber 32. As a result, the concentration of the protein will decrease. Alternatively, if the programmable logic controller 20 determines that the concentration of the protein is below the set point, it will control the electronic back-pressure valve 84 to close and increase the pressure in the concentrate sub-chamber 32. As a result, the concentration of the protein will increase.

A system that embodies the present invention can be constructed on skids at a central location and then shipped to its destination for final assembly and implementation. Construction in this manner is advantageous because it eliminates the need for duplicative construction resources and thus reduces the cost of constructing the system.

Although the description of the preferred embodiment and method have been quite specific, it is contemplated that various modifications could be made without deviating from the spirit of the present invention. Accordingly, it is intended that the scope of the present invention be dictated by the appended claims, rather than by the description of the preferred embodiment and method.

The claimed invention is:

1. A method of forming a whey protein concentrate, the concentrate having a predetermined concentration of a protein component in the concentrate, the method comprising the steps of:
   filtering a fluid thereby separating the fluid into a permeation and the concentrate;
   passing at least some of the concentrate through a spectrometric testing apparatus;
   determining the concentration of the protein component in the concentrate; and
   if concentration of the protein component is greater than a predetermined concentration, decreasing the concentration of the protein component to the predetermined concentration by feeding permeation into the concentrate.

2. The method of claim 1 comprising the additional step of increasing the concentration of the protein component to the predetermined concentration, if concentration of the protein component is less than the predetermined concentration.

3. The method of claim 1 wherein the step of determining the concentration of the protein component in the concentrate includes the step of continuously bleeding off a stream of the concentrate for sampling the protein component in the concentrate.

4. The method of claim 3 wherein the step of determining the concentration of the protein component in the concentrate further includes the step of periodically determining the concentration of the protein component in the sample.

5. The method of claim 1 wherein the concentrate includes a plurality of solids and the step of determining the concentration of the component includes the step of determining the ratio between the amount of the protein component in the concentrate and the total amount of solids in the concentrate.

6. The method of claim 1 wherein the protein component is a first component, the concentrate includes a second component and a plurality of solids, the step of determining the concentration of the protein component includes the step of determining the ratio between the amount of the first component in the concentrate and the amount of the second component in the concentrate.

7. The method of claim 1 wherein the concentrate is a liquid, the-method comprising the additional step of removing liquid from the concentrate.

8. The method of claim 7 wherein the step of removing liquid from the concentrate includes the steps of evaporating the liquid and then drying the concentrate, thereby causing the solids to form a powder.

9. The method of claim 1 wherein the fluid is a dairy product.

10. The method of claim 1 wherein a stream of concentrate is formed, the step of determining the concentration of the protein component including the step of taking a sample from the stream of concentrate, and the step of decreasing the concentration of the protein component includes the step of feeding permeation into the protein concentrate upstream from where the sample is taken.

11. A system for producing a concentrate from a fluid containing a component, the system comprising:
   a filter configured to receive the fluid and to separate the fluid into the concentrate and a permeate;

a first conduit in fluid communication with the filter and arranged to receive the concentrate;

a second conduit in fluid communication with the filter and arranged to receive permeate;

a valve in fluid communication between the first and second conduits;

a concentrate conduit in fluid communication with the first and second conduit and arranged to produce a resultant mixture at a pre-determined protein concentration;

a measuring device in fluid communication with the concentration conduit and configured to measure the concentration of the protein component within the concentrate, wherein the measuring device is a spectrometric testing apparatus; and a controller in electrical communication with the measuring device and the valve, the controller being configured to adjust the valve thereby adjusting the concentration of the concentrate.

12. The system of claim 11 wherein the controller is further configured to determine the concentration of the protein component in the concentrate and to control the valve to open and dilute the concentrate upon determining that the concentration of the protein component is greater than a predetermined concentration.

13. The system of claim 11 wherein the controller is further configured to close the valve upon determining that the concentration of the protein component is below a predetermined concentration.

14. The system of claim 11 wherein the valve includes an electronic actuator.

15. The system of claim 11 wherein the filter has a chamber and a semipermeable membrane dividing the chamber into a concentrate sub-chamber and a permeate sub-chamber.

16. A method of forming a concentrate, the concentrate having a predetermined concentration of a protein in the concentrate, the method comprising the steps of:

filtering a fluid thereby separating the fluid into a permeation and the concentrate;

automatically determining the concentration of the protein in the concentrate; and if concentration of the protein is greater than a predetermined concentration, decreasing the concentration of the protein to the predetermined concentration by feeding permeation into the concentrate.

* * * * *